US011457873B2

(12) United States Patent
Liu et al.

(10) Patent No.: US 11,457,873 B2
(45) Date of Patent: Oct. 4, 2022

(54) METHOD AND APPARATUS FOR IDENTIFYING HOMOLOGY OF PHYSIOLOGICAL SIGNALS

(71) Applicant: SHENZHEN MINDRAY BIO-MEDICAL ELECTRONICS CO., LTD., Shenzhen (CN)

(72) Inventors: Sanchao Liu, Shenzhen (CN); Jianwei Su, Shenzhen (CN); Zehui Sun, Shenzhen (CN); Bailei Sun, Shenzhen (CN); Wenyu Ye, Shenzhen (CN); Lihan Liu, Shenzhen (CN); Ming Li, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 118 days.

(21) Appl. No.: 16/672,640

(22) Filed: Nov. 4, 2019

(65) Prior Publication Data
US 2020/0060625 A1   Feb. 27, 2020

Related U.S. Application Data

(63) Continuation of application No. PCT/CN2017/110350, filed on Nov. 10, 2017.

(30) Foreign Application Priority Data

May 3, 2017 (CN) .......................... 201710304322.9

(51) Int. Cl.
*A61B 5/00* (2006.01)

(52) U.S. Cl.
CPC .......... *A61B 5/7264* (2013.01); *A61B 5/7257* (2013.01)

(58) Field of Classification Search
CPC . A61B 5/7264; A61B 5/7257; A61B 5/14551; A61B 5/021; A61B 5/318; A61B 5/7246; A61B 5/02055
See application file for complete search history.

(56) References Cited

U.S. PATENT DOCUMENTS

| 5,719,950 A | 2/1998 | Osten et al. | |
|---|---|---|---|
| 2003/0135097 A1* | 7/2003 | Wiederhold | A61B 5/02055 600/301 |

(Continued)

FOREIGN PATENT DOCUMENTS

| CN | 1568158 A | 1/2005 |
|---|---|---|
| CN | 1931091 A | 3/2007 |

(Continued)

OTHER PUBLICATIONS

First Office Action issued in related Chinese Application No. 201710304322.9, dated Sep. 24, 2020, 11 pages.

(Continued)

*Primary Examiner* — Brian T Gedeon
*Assistant Examiner* — Joshua Andrew Schum-Houck
(74) *Attorney, Agent, or Firm* — Bayes PLLC

(57) ABSTRACT

One variation of a method for identifying homology of physiological signals comprises: receiving signal data of two different types of physiological signals; performing waveform matching on the signal data of the two different types of physiological signals to determine waveform matching information in the signal data of the two types of physiological signals; calculating an associative feature between the signal data of the two different types of physiological signals according to the waveform matching information; calculating a homology reference coefficient corresponding to the two different types of physiological signals according to the associative feature; and determining that the two different types of physiological signals are homologous (Continued)

when the homology reference coefficient is greater than a preset value.

21 Claims, 10 Drawing Sheets

(56) References Cited

U.S. PATENT DOCUMENTS

| | | | | |
|---|---|---|---|---|
| 2004/0210146 A1* | 10/2004 | Diab | ............... | H04B 1/123 |
| | | | | 600/502 |
| 2005/0281439 A1* | 12/2005 | Lange | ............... | A61B 5/35 |
| | | | | 382/115 |
| 2011/0015532 A1* | 1/2011 | Koertge | ............... | A61B 5/30 |
| | | | | 600/509 |
| 2014/0188770 A1* | 7/2014 | Agrafioti | ............... | A61B 5/7267 |
| | | | | 706/13 |
| 2015/0065830 A1* | 3/2015 | Karp | ............... | A61B 5/02416 |
| | | | | 600/331 |
| 2016/0183812 A1* | 6/2016 | Zhang | ............... | A61B 5/117 |
| | | | | 600/301 |
| 2016/0191517 A1* | 6/2016 | Bae | ............... | H04L 63/0861 |
| | | | | 726/7 |
| 2017/0027464 A1* | 2/2017 | Cole | ............... | A61B 5/7207 |

FOREIGN PATENT DOCUMENTS

| | | |
|---|---|---|
| CN | 101773394 A | 7/2010 |
| CN | 101933811 A | 1/2011 |
| CN | 102231213 A | 11/2011 |
| CN | 103690152 A | 4/2014 |
| CN | 104054038 A | 9/2014 |
| CN | 104939820 A | 9/2015 |
| CN | 105740680 A | 7/2016 |
| CN | 105787420 A | 7/2016 |
| CN | 110312466 A | 10/2019 |

OTHER PUBLICATIONS

First Office Action issued in related Chinese Application No. 201780086365.2, dated Jul. 5, 2021, 9 pages.

* cited by examiner

METHOD AND APPARATUS FOR IDENTIFYING HOMOLOGY OF PHYSIOLOGICAL SIGNALS

CROSS-REFERENCE TO RELATED APPLICATIONS

This application is a continuation of PCT Application NO. PCT/CN2017/110350, filed Nov. 10, 2017, entitled "METHOD AND DEVICE FOR IDENTIFYING HOMOLOGY OF PHYSIOLOGICAL SIGNALS," which claims the benefit of priority to Chinese Patent Application No. 201710304322.9, filed on May 3, 2017, the entire contents of which are incorporated herein by reference.

TECHNICAL FIELD

The present disclosure relates to the technical field of medical instrument control, and in particular, to a method and an apparatus for identifying homology of physiological signals.

BACKGROUND

With the development of medical technology and the development of terminal technology, the function of a monitor for detecting various physiological conditions of a patient has also developed from monitoring of a single physiological signal to monitoring of a variety of physiological signals; the method for analyzing physiological signals of a patient has also developed from single signal analysis to multi-parameter fusional analysis, so as to improve the reliability and accuracy of analysis results. That is, the same monitor can monitor a variety of physiological signals of a patient, for example, detect a plurality of parameters such as electrocardiograms and blood pressure and blood oxygen signals of the patient, and analyze and decide the current physical conditions of the user according to acquired observed data of the plurality of parameters, thereby improving the reliability and accuracy of analysis results as compared with the solution of analyzing the observation result of a single current physiological signal of the user.

However, although the monitor can simultaneously monitor a plurality of physiological parameters of a patient and perform fusional analysis to reduce false reports or missing reports of the monitor, in the shortage of monitors or in other special cases, one monitor may also be used to monitor different types of physiological signals of two or a plurality of patients. For example, monitor A is used to monitor electrocardiograms of patient B, and meanwhile, monitor blood pressure and blood oxygen signals of patient C. However, an existing monitor cannot determine whether a variety of signals currently detected originate from the same patient, and while performing multi-parameter fusional analysis, the existing monitor can only perform analysis according to all signals detected by the current instrument instead of distinguishing between patients from which different signals originate. That is, once a monitor is used to monitor physiological signals of more than one patient, the monitor performs analysis according to different types of physiological signals of the plurality of patients during fusional analysis. Since the variety of physiological signals used for fusional analysis originate from different patients, and the patients differ in specific conditions, serious false reports or missing reports may occur in analysis results, causing a significant decrease in the reliability of multi-parameter fusional analysis.

SUMMARY

The present disclosure includes a method and an apparatus for identifying homology of physiological signals.

In one embodiment, a method for identifying homology of physiological signals comprises:
receiving signal data of two different types of physiological signals;
performing waveform matching on the signal data of the two different types of physiological signals to determine waveform matching information in the signal data of the two types of physiological signals;
calculating an associative feature between the signal data of the two different types of physiological signals according to the waveform matching information;
calculating a homology reference coefficient corresponding to the two different types of physiological signals according to the associative feature; and
determining that the two different types of physiological signals are homologous when the homology reference coefficient is greater than a preset value.

Optionally, in one embodiment, calculating an associative feature between the signal data of the two different types of physiological signals according to the waveform matching information comprises:
determining matching peaks in the two different types of physiological signals according to the waveform matching information, calculating a difference sequence of time points corresponding to the matching peaks in the two different types of physiological signals, and using the difference sequence as the associative feature between the signal data of the two different types of physiological signals. Optionally, in one embodiment, after receiving signal data of two different types of physiological signals, the method further comprises:
performing high-pass filtering and low-pass filtering on the signal data of the two different types of physiological signals.

Optionally, in one embodiment, after receiving signal data of two different types of physiological signals, the method further comprises:
separately extracting feature data of the signal data of the two different types of physiological signals;
calculating a signal quality parameter corresponding to the feature data according to a preset signal quality parameter calculation formula;
when the signal quality parameter does not meet a preset signal quality parameter threshold, determining that the signal data of the physiological signal corresponding to the signal quality parameter is invalid; and
when the signal quality parameter meets the preset signal quality parameter threshold, executing the step of performing waveform matching on the signal data of the two different types of physiological signals.

Optionally, in one embodiment, after separately extracting feature data of the signal data of the two different types of physiological signals, the method further comprises:
for any type of physiological signal, determining a signal type of the physiological signal, and determining a single-signal parameter type corresponding to the signal type;
calculating a single-signal parameter corresponding to the physiological signal according to a preset single-signal parameter calculation formula and the feature data;

deciding whether the single-signal parameter meets a preset single-signal parameter threshold;

when the single-signal parameter meets the preset single-signal parameter threshold, executing the step of performing waveform matching on the signal data of the two different types of physiological signals; and when the single-signal parameter does not meet the preset single-signal parameter threshold, generating prompt information of signal abnormality and prompting a user.

Optionally, in one embodiment, before the performing waveform matching on the signal data of the two different types of physiological signals, the method further comprises:

for the signal data of the two different types of physiological signals, deciding whether a data volume size of the signal data is greater than or equal to a preset data volume threshold, and if yes, then executing the step of performing waveform matching on the signal data of the two different types of physiological signals; if not, then continuing executing the step of receiving signal data of two different types of physiological signals.

Optionally, in one embodiment, calculating a homology reference coefficient corresponding to the two different types of physiological signals according to the associative feature further comprises:

calculating the homology reference coefficient corresponding to the two different types of physiological signals according to a preset homology reference coefficient calculation formula and the difference sequence.

Optionally, in one embodiment, calculating a homology reference coefficient corresponding to the two different types of physiological signals according to the associative feature further comprises:

calculating a mean or mean square error of the difference sequence to serve as the homology reference coefficient corresponding to the two different types of physiological signals.

Optionally, in one embodiment, before the performing waveform matching on the signal data of the two different types of physiological signals, the method further comprises:

separately performing Fourier transform on the signal data of the two different types of physiological signals to obtain transformed signal data; and the performing waveform matching on the signal data of the two different types of physiological signals is specifically:

performing waveform matching on the transformed signal data corresponding to the signal data of the two different types of physiological signals.

In one embodiment, an apparatus for identifying homology of physiological signals comprises:

a signal data receiving module, configured to receive signal data of two different types of physiological signals;

a waveform matching module, configured to perform waveform matching on the signal data of the two different types of physiological signals to determine waveform matching information in the signal data of the two types of physiological signals;

an associative feature acquisition module, configured to calculate an associative feature between the signal data of the two different types of physiological signals according to the waveform matching information;

a homology reference coefficient calculation module, configured to calculate a homology reference coefficient corresponding to the two different types of physiological signals according to the associative feature; and a homology identification module, configured to determine that the two different types of physiological signals are homologous when the homology reference coefficient is greater than a preset value.

Optionally, in one embodiment, the associative feature acquisition module is further configured to determine matching peaks in the two different types of physiological signals according to the waveform matching information, calculate a difference sequence of time points corresponding to the matching peaks in the two different types of physiological signals, and use the difference sequence as the associative feature between the signal data of the two different types of physiological signals.

Optionally, in one embodiment, the apparatus further comprises a data preprocessing module, configured to perform high-pass filtering and low-pass filtering on the signal data of the two different types of physiological signals.

Optionally, in one embodiment, the apparatus further comprises a signal quality parameter calculation module, configured to separately extract feature data of the signal data of the two different types of physiological signals; calculate a signal quality parameter corresponding to the feature data according to a preset signal quality parameter calculation formula; when the signal quality parameter does not meet a preset signal quality parameter threshold, determine that the signal data of the physiological signal corresponding to the signal quality parameter is invalid; and when the signal quality parameter meets the preset signal quality parameter threshold, invoke the waveform matching module.

Optionally, in one embodiment, the apparatus further comprises a single-signal parameter calculation module, configured to, for any type of physiological signal, determine a signal type of the physiological signal, and determine a single-signal parameter type corresponding to the signal type; calculate a single-signal parameter corresponding to the physiological signal according to a preset single-signal parameter calculation formula and the feature data; decide whether the single-signal parameter meets a preset single-signal parameter threshold; when the single-signal parameter meets the preset single-signal parameter threshold, execute the operation of performing waveform matching on the signal data of the two different types of physiological signals; and when the single-signal parameter does not meet the preset single-signal parameter threshold, generate prompt information of signal abnormality and prompt a user.

Optionally, in one embodiment, the apparatus further comprises a buffer filling module, configured to, for the signal data of the two different types of physiological signals, decide whether a data volume size of the signal data is greater than or equal to a preset data volume threshold, and when the data volume size of the signal data is greater than or equal to the preset data volume threshold, invoke the waveform matching module; when the data volume size of the signal data is less than the preset data volume threshold, invoke the signal data receiving module.

Optionally, in one embodiment, the homology reference coefficient calculation module is further configured to calculate the homology reference coefficient corresponding to the two different types of physiological signals according to a preset homology reference coefficient calculation formula and the difference sequence.

Optionally, in one embodiment, the homology reference coefficient calculation module is further configured to calculate a mean or mean square error of the difference sequence to serve as the homology reference coefficient corresponding to the two different types of physiological signals.

Optionally, in one embodiment, the apparatus further comprises a signal data transform module, configured to separately perform Fourier transform on the signal data of the two different types of physiological signals to obtain transformed signal data; and the waveform matching module is further configured to perform waveform matching on the transformed signal data corresponding to the signal data of the two different types of physiological signals.

The implementation of the embodiments of the present disclosure will have the following beneficial effects:

by adopting the aforementioned method and apparatus for identifying homology of physiological signals, when a monitor detects signal data of a plurality of different types of physiological signals, an associative feature of the detected signal data of the different types of physiological signals is extracted and calculated to determine the magnitude of a homology reference parameter that can identify the likelihood of two different types of physiological signals being homologous, so as to decide whether the two physiological signals are homologous. That is, homology analysis can be automatically performed on a plurality of items of data detected by the monitor, so as to avoid inaccurate analysis results caused by the fact that whether the detected data originates from the same patient cannot be determined while performing fusional analysis on a plurality of items of data detected by the monitor when the monitor simultaneously detects physiological data of different patients, thereby improving the accuracy and reliability of data analysis results.

BRIEF DESCRIPTION OF THE DRAWINGS

To illustrate the technical solutions in the embodiments of the present disclosure or in the prior art more clearly, the drawings to be used in the description of the embodiments or the prior art will be introduced briefly as follows. It is apparent that the drawings in the following description are merely some embodiments of the present disclosure. For those of ordinary skill in the art, other drawings can be obtained according to these drawings without any creative efforts.

The drawings are as follows.

DETAILED DESCRIPTION

The technical solutions in embodiments of the present disclosure will be described clearly and completely as follows in conjunction with the drawings in the embodiments of the present disclosure. It is apparent that the described embodiments are only some, rather than all, of the embodiments of the present disclosure. All other embodiments obtained by those of ordinary skill in the art based on the embodiments in the present disclosure without any creative efforts fall within the protection scope of the present disclosure.

In order to solve the technical problem of low reliability due to the fact that while performing multi-parameter fusional analysis on a plurality of physiological signals detected by a monitor, whether the current plurality of physiological signals originate from the same patient cannot be determined, a method for identifying homology of physiological signals is provided in some embodiments of the disclosure. The implementation of the method may depend on a computer program that may run on a computer system based on a Von Neumann architecture. The computer program may be an application for analyzing homology of physiological signals or an application for analyzing data homology based on data analysis of a monitor. The computer system may be a terminal device such as a monitor for running the aforementioned computer program.

In this embodiment, the same monitor can monitor relevant data of a plurality of different types of physiological signals, for example, simultaneously monitor a plurality of physiological signals that can be continuously measured, such as an electrocardiogram, a blood pressure signal, and a blood oxygen signal of a patient. It should be noted that in this embodiment, the physiological signals are limited to physiological signals that can be continuously monitored, because only data corresponding to continuous signals can be analyzed for historical trends and illness monitoring. That is, the monitor continuously monitors a plurality of different types of physiological signals of a patient and acquires corresponding signal data for illness analysis.

In the case of operational errors by medical staff or equipment shortage, one monitor may also be used to monitor physiological signals of a plurality of different patients. In this case, each type of detected physiological signal needs to be distinguished from others to determine whether they belong to the same patient, so as to avoid fusional analysis on physiological signals of a plurality of different patients and production of unreliable results.

Figure 1:
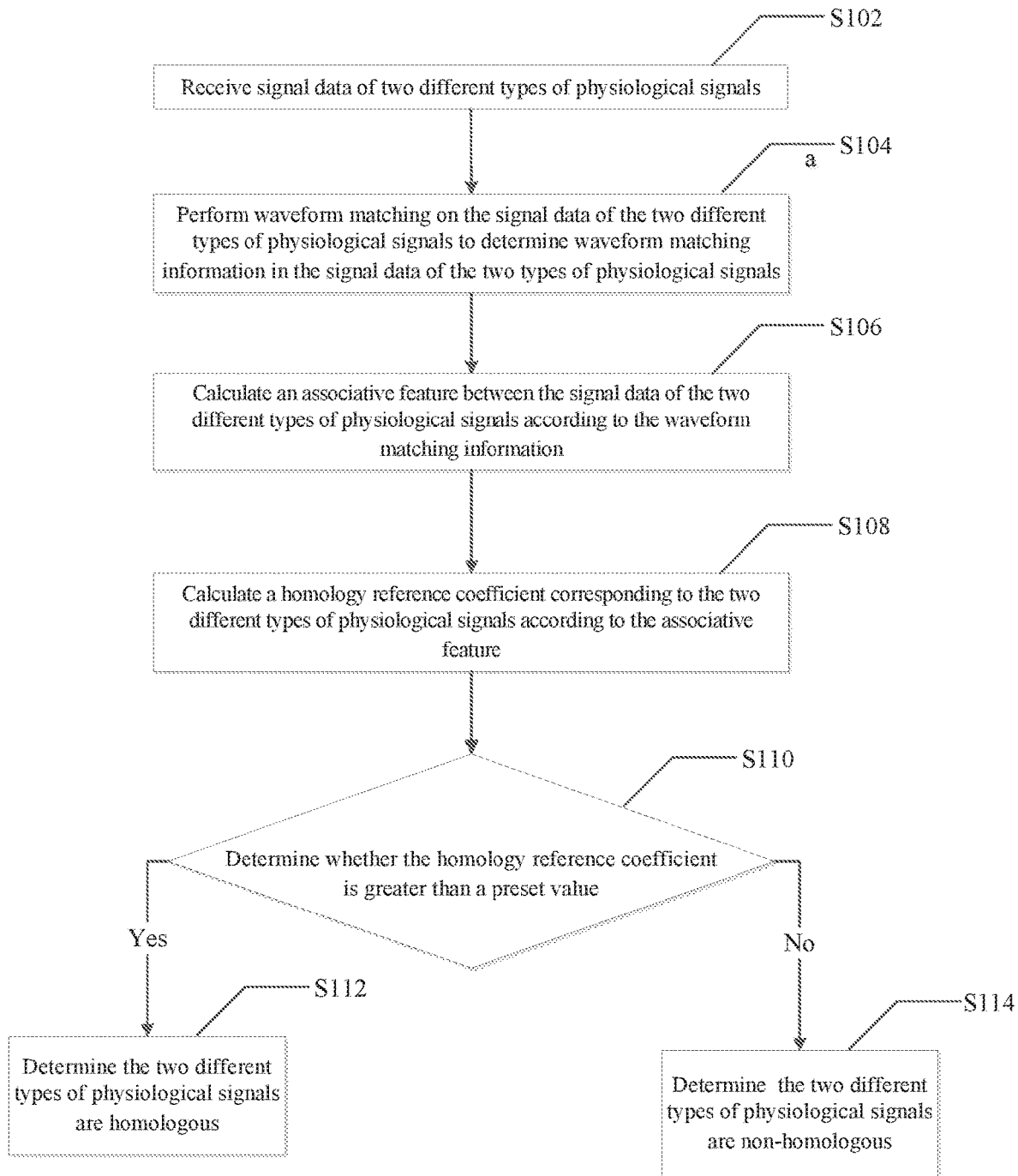
FIG. 1 is a schematic flowchart of a method for identifying homology of physiological signals in one embodiment.

Specifically, as shown in FIG. 1, the aforementioned method for identifying homology of physiological signals includes the following steps S102 to S114:

step S102: Receive signal data of two different types of physiological signals.

In this embodiment, the analysis on whether signal data of different types of physiological signals is homologous is analysis on whether signal data of two different types of physiological signals is homologous. When a monitor detects signal data of more than two types of physiological signals, homology analysis may be separately performed on a plurality of pieces of signal data in pairs, or homology analysis may be performed on all detected signal data.

The different types of the physiological signals refer to different types or kinds of physiological signals at least having different measuring principles. For example, one is an electrocardiogram, and the other is a blood oxygen signal, which are two different types of physiological signals. For convenience of description, the two different types of physiological signals monitored by the monitor are respectively referred to as a physiological signal A and a physiological signal B.

In this embodiment, upon detecting physiological signals of patients fed into a data analysis module in the monitor or sent to any other terminal device dedicated for data analysis, the monitor acquires data corresponding to the detected physiological signals and determines whether signal data of the different types of detected physiological signals is homologous.

Step S104: Perform waveform matching on the signal data of the two different types of physiological signals to determine waveform matching information in the signal data of the two types of physiological signals.

In this embodiment, the mode of performing waveform matching on the signal data of the two different types of physiological signals may be performing matching on waveforms in the signal data of the two different types of physiological signals. For example, in the same waveform image presentation page, a waveform corresponding to signal data of one physiological signal is in the upper part, while a waveform corresponding to signal data of the other physiological signal is correspondingly presented in the lower part, so as to determine the mode of waveform matching therebetween.

Under normal conditions, a peak of the physiological signal A corresponds to a peak of the physiological signal B; while under the influence of other external factors, peaks of the physiological signal A cannot correspond one-to-one to peaks of the physiological signal B. By waveform matching, a specific peak of the physiological signal B to which a peak of the physiological signal A corresponds can be determined, so as to determine a correspondence between the waveforms in the signal data of the two different types of physiological signals.

Figure 2:
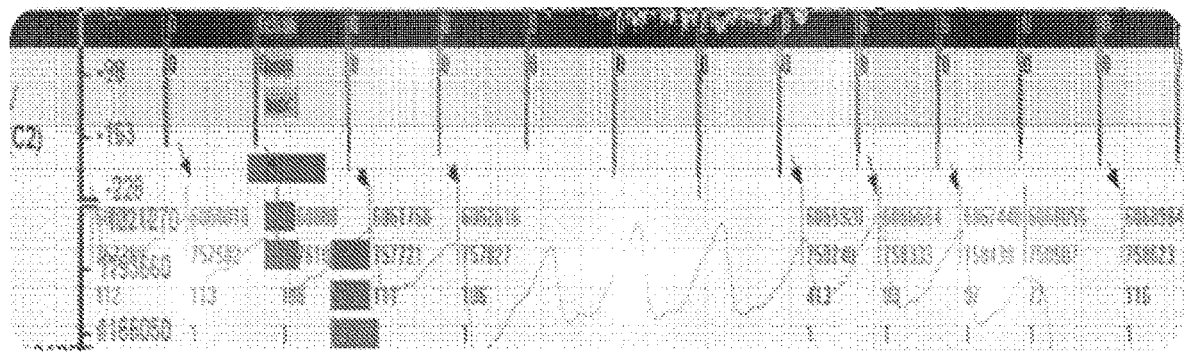
FIG. 2 is a schematic diagram of waveform matching on two different types of physiological signals in one embodiment.

Using the determining of a matching relationship between peaks as an example, in the application scenario shown in FIG. 2, FIG. 2 is an instance diagram of waveform matching, where one is an electrocardiogram (ECG, an electrophysiological signal), and one is a blood oxygen signal (SPO2, a mechanical physiological signal). When the monitor simultaneously monitors the electrocardiogram and the blood oxygen signal, the electrocardiogram and the blood oxygen signal that are detected may be simultaneously presented in a data display window of the monitor. In FIG. 2, the correspondence between peaks of the electrocardiogram and the blood oxygen signal is provided. That is, the matching mode of peaks in signal data corresponding to the electrocardiogram and the blood oxygen signal is determined, and a specific peak in the signal data of the blood oxygen signal to which each peak of the electrocardiogram should correspond is determined.

Optionally, in this embodiment, before waveform matching is performed, deciding whether waveforms in the acquired signal data of the physiological signals are valid is further needed. For example, under temporary interference from external factors, part of the waveform in the detected signal data of the physiological signal may not match the waveform in the signal data of the other physiological signal. That is, some data in the detected signal data of the physiological signal is invalid.

Specifically, in one alternative embodiment, before performing waveform matching on the signal data of the two different types of physiological signals and determining waveform matching information in the signal data of the two types of physiological signals, it is further needed to determine that data in the signal data respectively corresponding to the physiological signal A and the physiological signal B is valid, namely, determine that data such as peaks or troughs in the signal data is valid.

Figure 3:
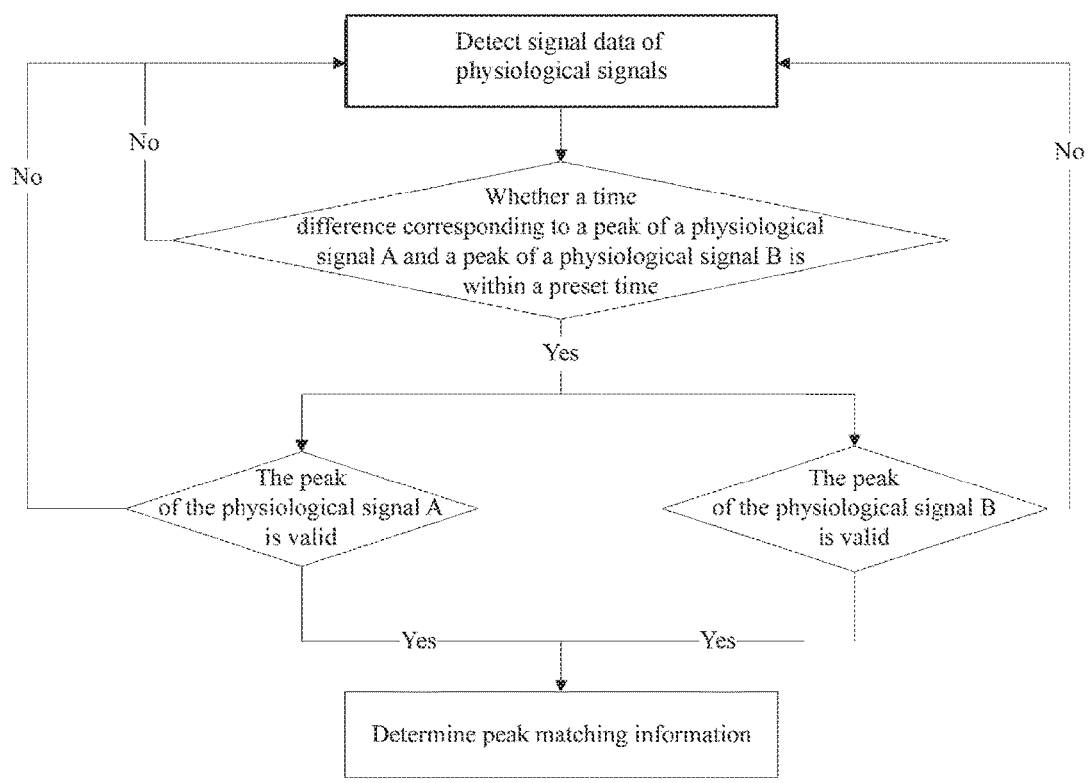
FIG. 3 is a schematic flowchart of waveform matching in one embodiment.

As shown in FIG. 3, when determining the aforementioned waveform matching information, it is needed to determine whether a time interval between timestamps corresponding to corresponding peaks in the signal data respectively corresponding to the physiological signal A and the physiological signal B is within a preset time, and if yes, then the two peaks match. Further, before determining the waveform matching information, deciding whether the detected signal data of the physiological signals is valid is further needed. For example, when the detected signal data has large errors under the influence of external signals during monitoring, then the corresponding signal data is invalid.

It should be noted that in this embodiment, many decision modes may exist to decide whether the detected signal data of the physiological signals is valid. For example, for the signal types of the physiological signals, calculating signal quality parameters corresponding to the signal types; or deciding whether the signal data of the physiological signals includes signal data satisfying a preset invalidity condition, or the like, is not limited in this embodiment.

Step S106: Calculate an associative feature between the signal data of the two different types of physiological signals according to the waveform matching information.

The associative feature refers to a feature between the physiological signal A and the physiological signal B having a typical physiological correspondence. For example, the waveforms corresponding to the signal data of the electrocardiogram and the blood oxygen signal are both related to conditions such as heart rates of the monitored patients. In this embodiment, the acquisition of the associative feature may be acquiring the feature between the physiological signal A and the physiological signal B having the typical physiological correspondence according to the waveform matching information of the signal data of the physiological signals in combination with other signal features (for example, a time interval between timestamps corresponding to matching peaks, or a time interval between peaks in the physiological signals) of the physiological signal A and the physiological signal B. Generally speaking, the associative feature can clearly show whether a plurality of different types of physiological signals are homologous.

In one specific embodiment, the step of calculating an associative feature between the signal data of the two different types of physiological signals according to the waveform matching information is specifically the following: determining matching peaks in the two different types of physiological signals according to the waveform matching information; calculating a difference sequence of time points corresponding to the matching peaks in the two different types of physiological signals; and using the difference sequence as the associative feature between the signal data of the two different types of physiological signals. That is, the associative feature is the difference sequence of the time points corresponding to the matching peaks in the two different types of physiological signals.

Specifically, the associative feature includes difference data between timestamps corresponding to the matching peaks in the physiological signal A and the physiological signal B. For example, in step S104, if it is determined that each peak included in the signal data of the physiological signal A matches a peak in the signal data of the physiological signal B, the two peaks are matching peaks. For example, as shown in FIG. 2, matching peaks in the signal data of the two physiological signals are determined. Then, time differences of timestamps respectively corresponding to all matching peaks are calculated to obtain a difference sequence. The difference sequence may indicate whether the correspondence between the physiological signal A and the physiological signal B changes. For example, when the physiological signal A is an electrocardiogram and the physiological signal B is a blood oxygen signal, their corresponding peaks or troughs are both related to heartbeats of the monitored patients. Thus, the calculated difference sequence should be a mean sequence (that is, each element in the sequence is equal). That is, in this embodiment, the difference sequence should be a sequence having small fluctuations.

It should be noted that in this embodiment, the associative feature may further include a difference sequence of time points corresponding to matching troughs in the two different types of physiological signals, or a sequence of cycle lengths between adjacent peaks or troughs in the signal data of the two different types of physiological signals.

Step S108: Calculate a homology reference coefficient corresponding to the two different types of physiological signals according to the associative feature.

In this embodiment, the homology reference coefficient may represent the likelihood of the two different types of physiological signals received in step S102 being homologous. For example, the value of the homology reference coefficient may be 0 to 100, and the larger the homology reference coefficient, the more likely the two different types of physiological signals are homologous.

In one specific embodiment, calculating a homology reference coefficient corresponding to the two different types of physiological signals according to the associative feature further includes: calculating the homology reference coefficient corresponding to the two different types of physiological signals according to a preset homology reference coefficient calculation formula and the difference sequence.

The homology reference coefficient corresponding to the two different types of physiological signals detected in step S102 is calculated according to each element included in the difference sequence of the time points corresponding to the matching peaks in the two different types of physiological signals and the preset homology reference coefficient. For example, a mean, a variance, a mean square error, or a minimum residual of the difference sequence is calculated, and the calculation result is used as the homology reference coefficient corresponding to the two different types of physiological signals.

It should be noted that in this embodiment, the calculation method for the homology reference coefficient is not limited to the aforementioned parameters such as the mean, variance, mean square error, or minimum residual of the difference sequence, but may also be any other parameters that can directly indicate whether the signal data of the two physiological signals is homologous.

Step S110: Decide whether the homology reference coefficient is greater than a preset value, and if yes, execute step S112 of determining that the two different types of physiological signals are homologous; if not, then execute step S114 of determining that the two different types of physiological signals are non-homologous.

The homology reference coefficient is a number, and the larger the number, the more likely the signal data of the two different types of physiological signals is homologous; on the contrary, the smaller the number, the less likely the signal data of the two different types of physiological signals originates from the same patient. For example, when the homology reference coefficient is 100, it is determined that the two different types of physiological signals are homologous; when the homology reference coefficient is 0, it is determined that the two different types of physiological signals are non-homologous.

In practice, a threshold of the homology reference coefficient may be set to 80, and when the calculated homology reference coefficient is greater than 80, it is determined that the two different types of physiological signals are homologous; on the contrary, then it is determined that the two different types of physiological signals are non-homologous.

Figure 4:
FIG. 4 is a schematic diagram of waveform matching on two different types of physiological signals that are homologous in one embodiment.
Figure 5:
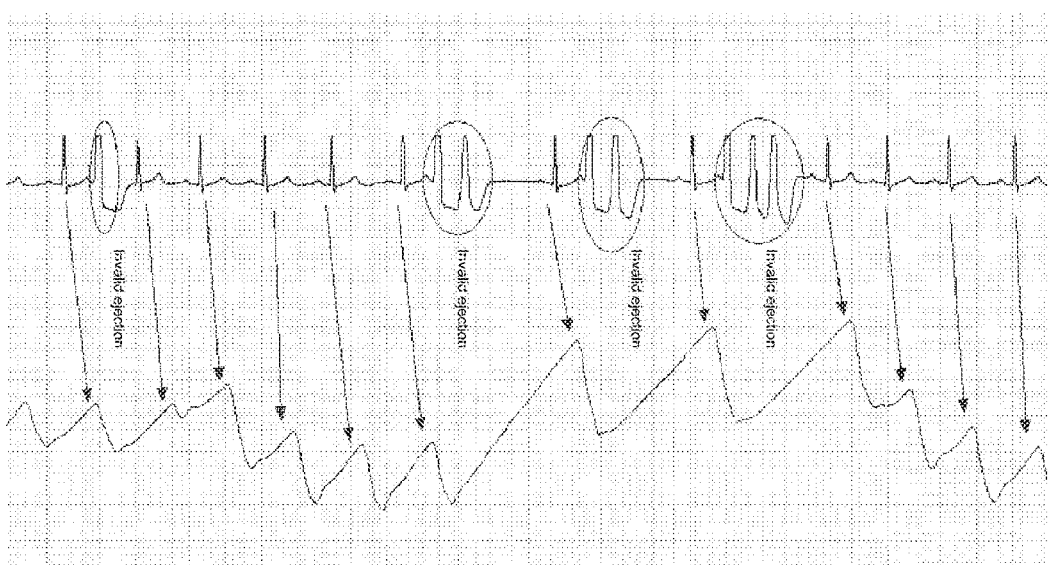
FIG. 5 is a schematic diagram of waveform matching on two different types of physiological signals that are homologous in one embodiment.

FIG. 4 and FIG. 5 provide schematic diagrams of waveform matching on two different types of physiological signals that are homologous. In FIG. 4, all peaks in signal data of the two physiological signals have one-to-one correspondence, and the correspondence does not change; in FIG. 5, all peaks in valid signal data of the two physiological signals have one-to-one correspondence, and the correspondence does not change.

Figure 6:
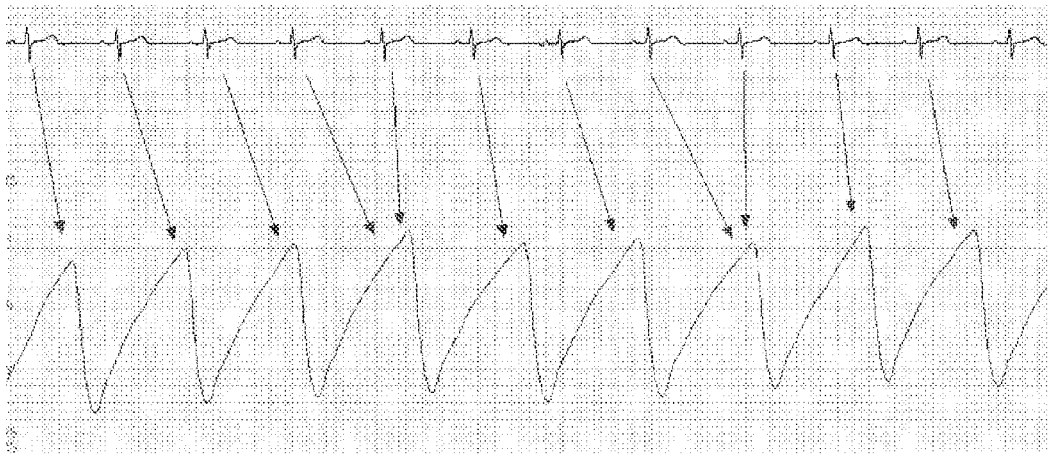
FIG. 6 is a schematic diagram of waveform matching on two different types of physiological signals that are non-homologous in one embodiment.

In another embodiment, as shown in FIG. 6, not all peaks in signal data of two physiological signals have one-to-one correspondence, and abnormality also occurs in the correspondence. In this case, it can be determined that the two physiological signals shown in FIG. 6 are non-homologous.

Steps S102 to S114 are deciding whether the two different types of detected physiological signals are homologous by calculating the homology reference coefficient of the two different types of physiological signals, step S102 is a step of signal collection, and steps S104 to S114 are a process of signal homology analysis.

It should be noted that in this embodiment, after the signal data of the physiological signals is received, an optional step further includes preprocessing the received signal data. Specifically, the preprocessing mode includes filtering the signal data. Specifically, after receiving signal data of two different types of physiological signals as mentioned above, the method further includes: performing high-pass filtering and low-pass filtering on the signal data of the two different types of physiological signals.

The high-pass filtering on the signal data may be implemented by a high-pass filter. After high-pass filtering is performed on the signal data, low-frequency signals lower than a preset threshold are blocked and weakened. That is, data lower than a preset frequency is attenuated, so as to eliminate low-frequency noise in the signal data of the physiological signals.

The low-pass filtering on the signal data may be implemented by a preset low-pass filter. After low-pass filtering is performed on the detected signal data, high-frequency signals higher than a preset threshold are blocked and weakened. That is, data higher than a preset frequency is attenuated, so as to eliminate high-frequency noise in the detected signal data of the physiological signals.

In this embodiment, high-pass filtering and low-pass filtering are performed on the detected signal data of the physiological signals, so that high-frequency noise and low-frequency noise in the detected signal data of the physiological signals can be filtered out, and baseline drift can be filtered out, thereby improving the reliability of the signal data.

For example, in one specific embodiment, high-pass filtering (with a cut-off frequency of 0.05 Hz) and low-pass filtering (with a cut-off frequency of 40 Hz) are performed on an electrocardiogram (ECG). In another specific embodiment, high-pass filtering (with a cut-off frequency of 0.3 Hz) and low-pass filtering (with a cut-off frequency of 5 Hz) are performed on a blood oxygen signal (SPO2).

The collection and analysis of the signal data of the physiological signals are both based on time-based change rules or signal features of the physiological signals, equivalent to extracting features of the signal data of the physiological signals in the time domain. In another embodiment, the process of feature extraction and calculation may also be performed based on features of the physiological signals in the frequency domain.

Specifically, in one alternative embodiment, before the performing waveform matching on the signal data of the two different types of physiological signals, the method further includes: separately performing Fourier transform on the signal data of the two different types of physiological signals to obtain transformed signal data, and the performing waveform matching on the signal data of the two different types of physiological signals is: performing waveform matching on the transformed signal data corresponding to the signal data of the two different types of physiological signals.

That is, after the signal data of the physiological signals is received, Fourier transform is performed on the received signal data, and signal data obtained after Fourier transform is transformed signal data. When operations such as waveform matching and feature extraction are performed, all operations performed use the transformed signal data after Fourier transform.

It should be noted that in this embodiment, the transform used in converting the signal data from signal data in the time domain to signal data in the frequency domain may not be only performed by Fourier transform, but may also be performed by any other transform that can transform time-domain data into frequency-domain data.

In another embodiment, any transform mode such as wavelet transform or cosine transform may also be used to transform the originally received signal data of the physiological signals before processing.

It should be noted that the aforementioned transform such as Fourier transform on the received signal data of the physiological signals may be performed after the signal data of the physiological signals is received or after the signal data is preprocessed, but needs to be performed before waveform matching is performed on the signal data.

In another alternative embodiment, for the detected signal data of the physiological signals or the preprocessed signal data, corresponding feature data thereof may further be extracted according to a preset feature extraction algorithm, and then the feature data is analyzed.

Specifically, after receiving signal data of two different types of physiological signals, the method further includes: separately extracting feature data of the signal data of the two different types of physiological signals. It should be noted that different types of physiological signals correspond to different feature data. For example, for an electrocardiogram (ECG), the process of extracting feature data corresponding to signal data thereof may be a process of detecting and classifying QRS complexes for the signal data, where the QRS complex reflects the electrical behavior of the heart when the ventricles contract and is the basis for automatic electrocardiogram analysis. For another example, for a blood oxygen signal (SPO2), the process of extracting feature data of signal data thereof is a process of monitoring a PLUS wave (pulse wave) corresponding to the signal data of SPO2, where the PLUS wave reflects the feature data of the blood oxygen signal.

After the feature data of the signal data of the physiological signals is extracted, feature analysis can be performed according to the feature data. For example, the feature data corresponding to the signal data of the physiological signals is used as the signal data of the physiological signals detected in step S102, so as to perform homology analysis in steps S104 to S114.

In another embodiment, corresponding data analysis is performed on feature data corresponding to signal data of a single physiological signal. For example, a signal quality parameter corresponding to the signal data of the physiological signal is calculated to decide whether the detected signal data meets preset quality criteria, and if the criteria are met, indicating that the detected signal data is up to standard and can be used for further data analysis or other operations; on the contrary, if the criteria are not met, then indicating that the detected signal data is substandard, and if the signal data is used for further data analysis, obtained data analysis results may have large errors due to the substandard signal data, that is, the data analysis results have insufficient reliability.

Specifically, after the feature data of the signal data of the physiological signal is extracted, a signal quality parameter corresponding to the feature data is calculated according to a preset signal quality parameter calculation formula; when the signal quality parameter does not meet a preset signal quality parameter threshold, it is determined that the signal data of the physiological signal corresponding to the signal quality parameter is invalid; and when the signal quality parameter meets the preset signal quality parameter threshold, the step of performing waveform matching on the signal data of the two different types of physiological signals is executed.

The signal quality parameter (signal quality index, SQI) can reflect the level of the signal quality corresponding to the detected signal data of the physiological signal. Moreover, the value range of the signal quality parameter is 0 to 100, and the larger the signal quality parameter, the higher the quality of the corresponding signal data of the physiological signal. For example, the smaller a signal-to-noise ratio (SNR) of the signal data, the higher the signal quality parameter. The signal quality parameter can provide an objective evaluation for the quality of the detected signal data of the physiological signal.

In one specific embodiment, when the physiological signal is an electrocardiogram, corresponding feature data thereof is a QRS complex, and when calculating a signal quality parameter corresponding thereto, first, a signal-to-noise ratio (SNR) of the QRS complex may be calculated, and then the signal quality parameter corresponding to the electrocardiogram is calculated using the signal-to-noise ratio, or the signal-to-noise ratio is directly used as the signal quality parameter corresponding to the electrocardiogram.

In this embodiment, the signal quality parameter is calculated to decide whether the currently detected physiological signal satisfies a condition, and specifically, whether a signal quality parameter corresponding to signal data of the detected physiological signal meets a preset signal quality parameter threshold, and if yes, then it is determined that the signal data satisfies the preset condition and can be further processed. On the contrary, if the signal quality parameter corresponding to the signal data of the detected physiological signal does not meet the preset signal quality parameter threshold, then it indicates that the corresponding signal data of the physiological signal does not satisfy the preset condition, and if the signal data is used for further data analysis, large errors may be generated. Thus, the signal data of the physiological signal is deemed invalid.

In this embodiment, for the signal data of the detected physiological signal, it is needed to decide whether the signal data meets specific signal quality, and to further decide whether abnormality or any other situation exists. For example, for signal data corresponding to an electrocardiogram, deciding whether heart rate abnormality exists in the signal data is further needed, and if heart rate abnormality exists, then an alarm needs to be issued directly for prompt.

Specifically, after separately extracting feature data of the signal data of the two different types of physiological signals, the method further includes: for any type of physiological signal, determining a signal type of the physiological signal, and determining a single-signal parameter type corresponding to the signal type; calculating a single-signal parameter corresponding to the physiological signal according to a preset single-signal parameter calculation formula and the feature data; deciding whether the single-signal parameter meets a preset single-signal parameter threshold; and when the single-signal parameter does not meet the preset single-signal parameter threshold, generating prompt information of signal abnormality and prompting a user. Different types of physiological signals also correspond to different signal abnormalities or situations where a prompt needs to be given. For example, for a blood oxygen signal, the situation requiring a prompt is different from heart rate abnormality of an electrocardiogram; instead, a prompt is given when the blood oxygen is excessively low. Therefore, it is firstly needed to determine, according to a signal type of a physiological signal, a single-signal parameter type corresponding to the signal type, for example, calculating a heart rate for an electrocardiogram, and calculating a blood oxygen concentration for a blood oxygen signal.

After the single-signal parameter type to be calculated is determined, a single-signal parameter corresponding to a signal parameter of the detected physiological signal can be calculated according to a preset single-signal parameter calculation formula. It should be noted that in this embodiment, when calculating the single-signal parameter, the single-signal parameter may be calculated directly by using signal data of the physiological signal, or may be calculated by using extracted feature data corresponding to the signal data of the physiological signal.

In one specific embodiment, the signal type of the physiological signal is an electrocardiogram, the corresponding single-signal parameter type is heart rate, and the corresponding heart rate is calculated by using position information of a QRS complex in QRS complex data extracted for the signal data of the physiological signal.

In another specific embodiment, the signal type of the physiological signal is a blood oxygen signal, the corresponding single-signal parameter type is blood oxygen concentration, a corresponding pulse is calculated by using position information of a PLUS wave in PLUS wave data extracted for the signal data of the physiological signal, and the blood oxygen concentration corresponding to the blood oxygen signal is calculated according to a ratio of an alternating-current component to a direct-current component of the PLUS wave.

Further, in this embodiment, after a single-signal parameter corresponding to the signal data of the physiological signal is calculated, deciding whether the single-signal parameter satisfies a preset condition is needed, for example, deciding whether the single-signal parameter meets a preset single-signal parameter threshold. For example, both the heart rate exceeding a specific value and the heart rate being below a specific value are abnormalities. In this embodiment, for the signal type of each physiological signal, a single-signal parameter threshold corresponding to a corresponding single-signal parameter type is set for deciding whether an obtained single-signal parameter meets the single-signal parameter threshold. If the single-signal parameter meets the single-signal parameter threshold, then indicating that no abnormality or situation where a prompt needs to be given exists in the signal data of the currently detected physiological signal, and the method can proceed to the next step of homology analysis, on the contrary, if the single-signal parameter does not meet the single-signal parameter threshold, then indicating that abnormality or any other situation exists in the signal data of the currently detected physiological signal where a prompt needs to be given, and thus the user needs to be prompted to perform processing in time. For example, if the heart rate is excessively low, the user is prompted by issuing an alarm.

It should be noted that in this embodiment, when calculating the single-signal parameter, the single-signal parameter does not meet the preset single-signal parameter threshold, corresponding prompt information needs to be generated to prompt the user, and a choice may further be made on whether to continue with the homology analysis according to actual situations. The reason is as follows: in case of abnormality of the signal data of the physiological signal, some signal data has abnormality, while other signal data may or may not have abnormality. In this case, analyzing whether two different physiological signals are homologous is also needed, so as to improve the reliability of analysis on patient conditions.

To sum up, in this embodiment, for received signal data of physiological signals, before homology analysis is performed, a data analysis process for a single physiological signal, including a plurality of steps such as data preprocessing, feature data extraction, signal quality parameter calculation, and single-signal parameter calculation needs to be performed on the received signal data of the physiological signals. In this embodiment, the aforementioned process of data preprocessing, feature data extraction, signal quality parameter calculation, and single-signal parameter calculation for received signal data of a single physiological signal is the process of single-signal analysis.

Figure 7:
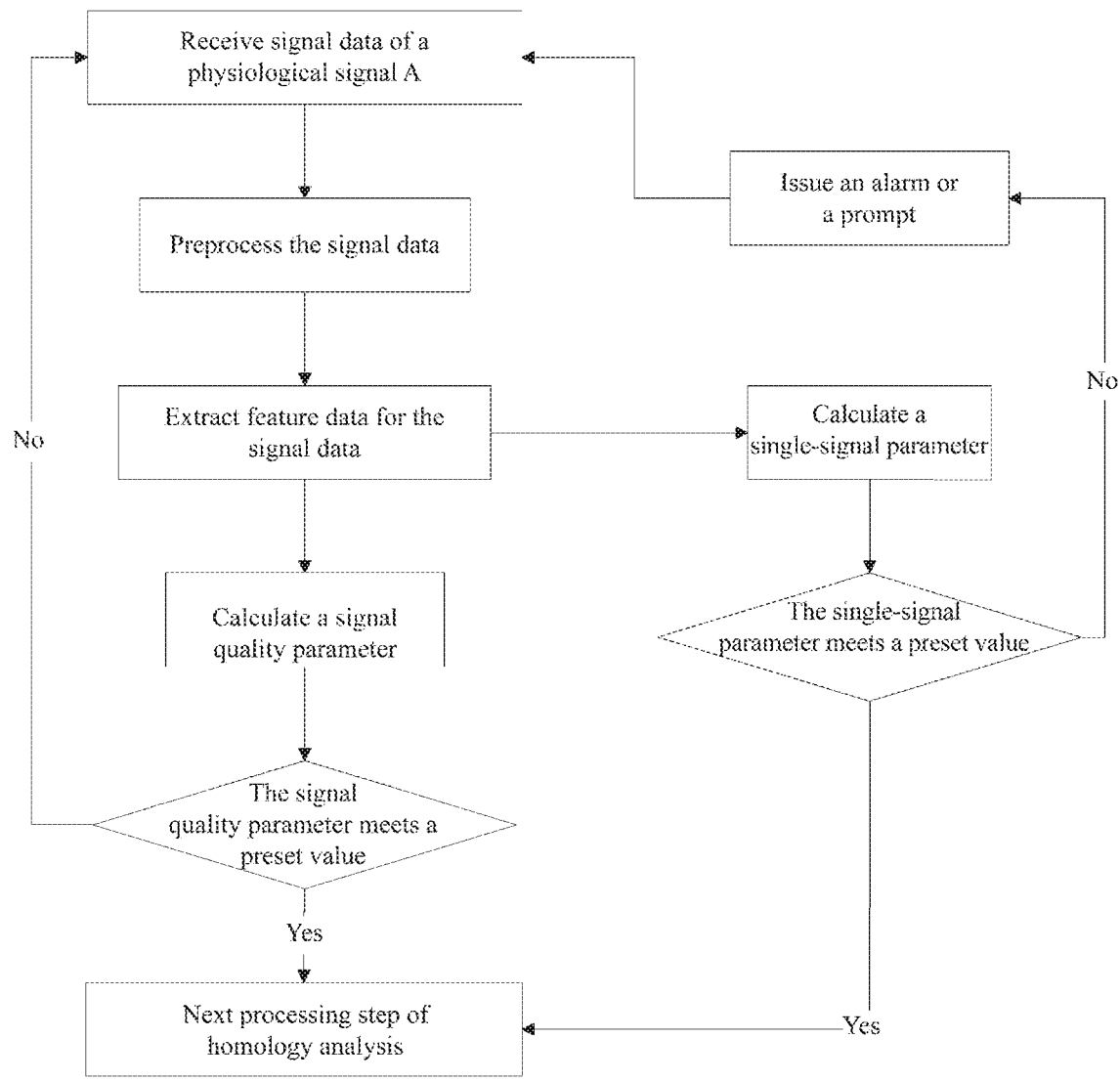
FIG. 7 is a schematic flowchart of single-signal analysis on a physiological signal in one embodiment.

As shown in FIG. 7, FIG. 7 shows a process of single-signal analysis on the physiological signal A. After signal data of a physiological signal of a patient is detected by a monitor, first, the signal data is preprocessed to improve the reliability of subsequent data analysis; then, feature data of the signal data is extracted, a corresponding signal quality parameter and single-signal parameter are separately calculated, and it is decided whether the calculated signal quality parameter and single-signal parameter meet preset conditions, and if they both meet the preset conditions, the method proceeds to the next step, for example, performing waveform matching and determining waveform matching information.

Figure 8:
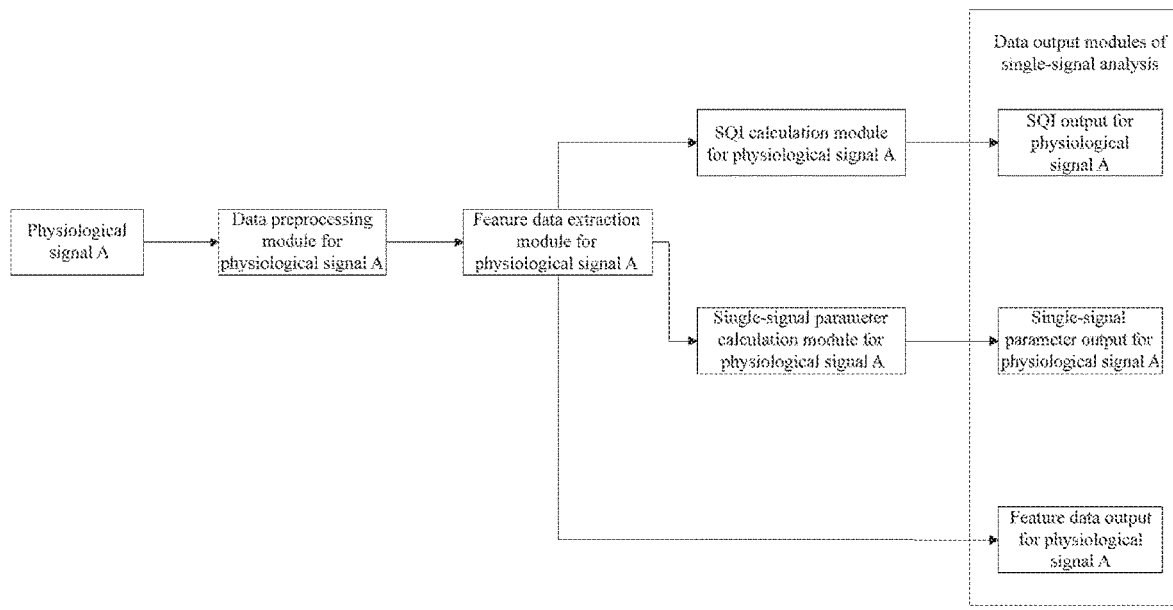
FIG. 8 is a schematic constitutional diagram of various modules that perform single-signal analysis on a physiological signal in one embodiment.

In the process of single-signal analysis, various steps or operations of single-signal analysis are all implemented by corresponding modules. For example, the process of preprocessing signal data of the physiological signal A is implemented by a data preprocessing module. As shown in FIG. 8, FIG. 8 shows a data relationship between various modules in the process of single-signal analysis.

In this embodiment, the physical condition of a patient is analyzed, for example, the development trend of a disease of the patient is analyzed according to signal data of a physiological signal of the patient that is detected by a monitor. No matter what data analysis method is used for analysis, relevant data of the patient in a period of time is required for accurate analysis. For example, when the data under analysis is only signal data of a physiological signal of the patient that is detected within 30 s; the detected signal data can only represent the patient's condition within the 30 s, which may be temporarily affected and cannot exactly represent patient conditions. Therefore, generally speaking, in order to improve the accuracy of analysis results of analyzing signal data of a physiological signal detected by the monitor, the signal data detected by the monitor further needs to reach a specific data volume in this embodiment.

Specifically, before the performing waveform matching on the signal data of the two different types of physiological signals, the method further includes: for the signal data of the two different types of physiological signals, deciding whether a data volume size of the signal data is greater than or equal to a preset data volume threshold, and if yes, executing the step of performing waveform matching on the signal data of the two different types of physiological signals; if not, continuing executing the step of receiving signal data of two different types of physiological signals.

For example, a data volume threshold is set, and detected data is analyzed only if a data volume corresponding to the detected signal data reaches or exceeds the data volume threshold. That is, homology analysis is performed on detected signal data of different types of physiological signals only if a data volume corresponding to the detected signal data reaches or exceeds the preset data volume threshold; otherwise, monitoring of the signal data of the physiological signals is continued to reach the preset data volume.

In one specific embodiment, buffer filling may be performed on the detected signal data of the physiological signals, and the storage size of a buffer is preset. Then, homology analysis is performed only after the detected signal data of the physiological signals fills the buffer and accumulates to a specific data volume. For example, when the detected signal data of the physiological signals overfills the buffer, waveform matching or data preprocessing is performed on the different types of detected physiological signals.

Figure 9:
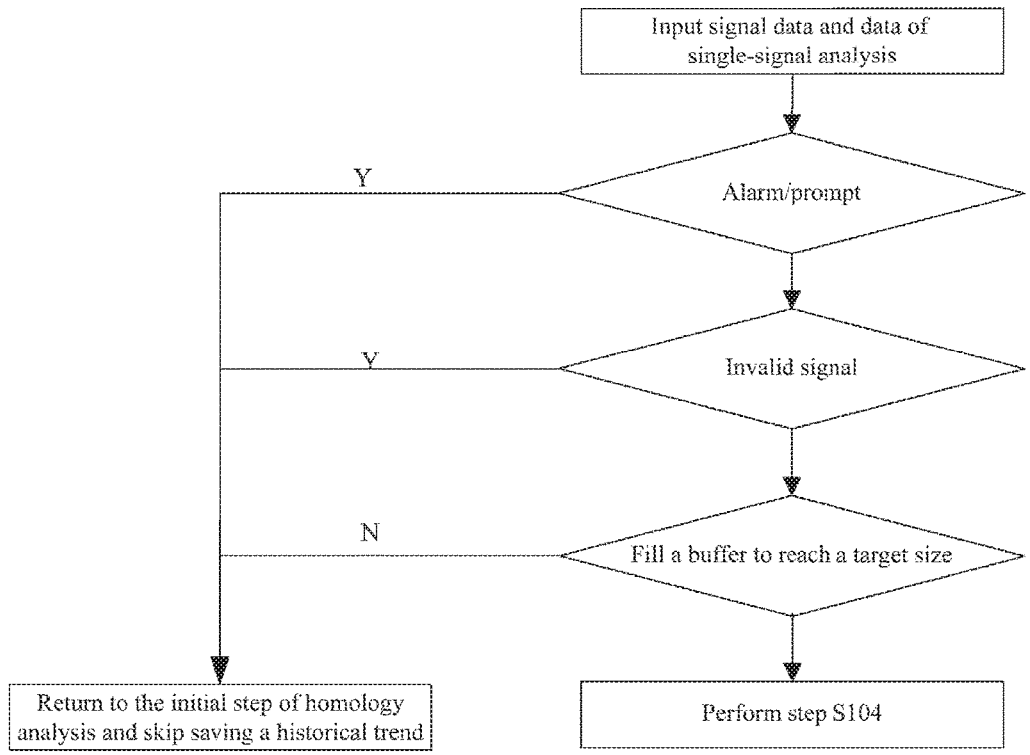
FIG. 9 is a schematic flowchart of buffer filling using a physiological signal in one embodiment.

For example, as shown in FIG. 9, after signal data of a physiological signal and corresponding feature data, signal quality parameter, and single-signal parameter are received, it can be determined whether the current signal data is valid or whether an alarm or a prompt needs to be given for the current signal data. In the special case that the signal data is valid and does not need any alarm or prompt, the signal data is used to fill the buffer, and when a preset data volume size is reached, the method proceeds to the next operational step, for example, step S104 is executed; on the contrary, the method returns to the monitoring of signal data of physiological signals, namely, returns to the initial step of homology analysis.

Figure 10:
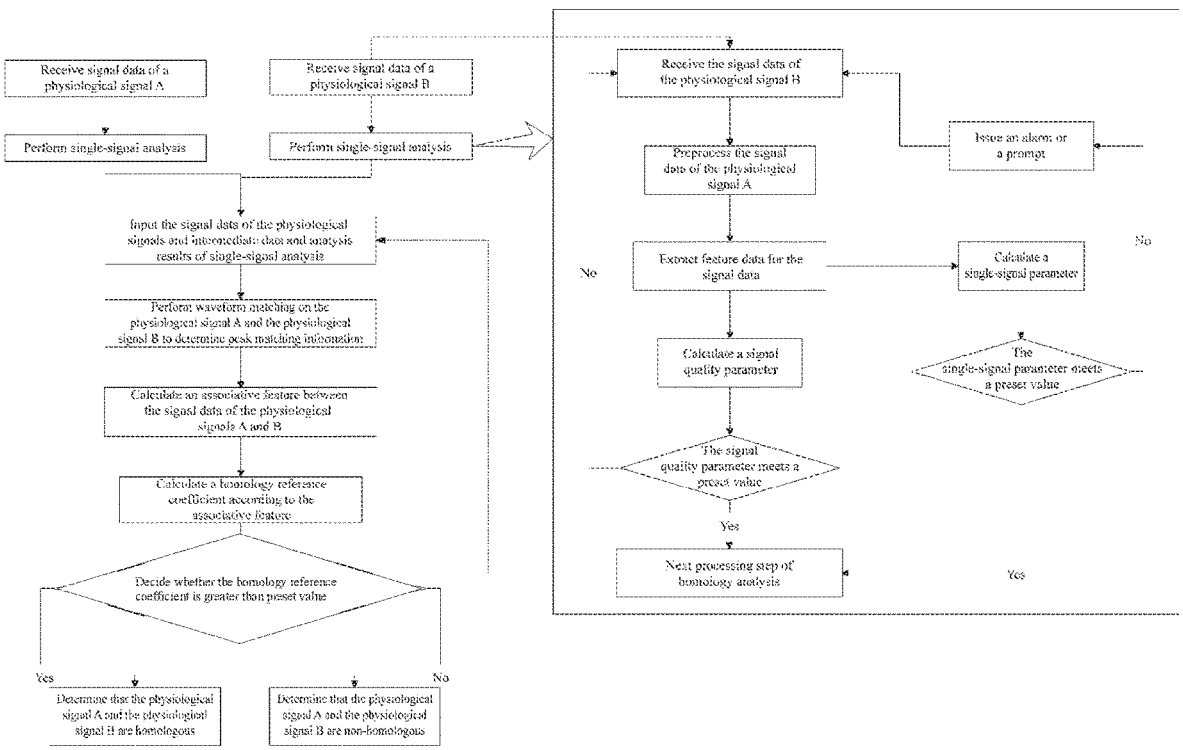
FIG. 10 is a schematic flowchart of identification of whether signal data of two different types of physiological signals is homologous in one embodiment.
Figure 11:
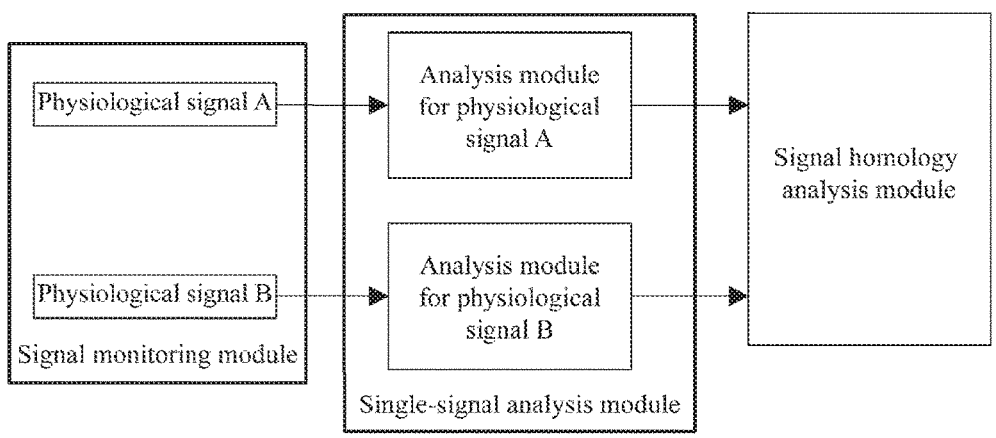
FIG. 11 is a schematic structural diagram of various modules that identify whether signal data of two different types of physiological signals is homologous in one embodiment.

In another embodiment, as shown in FIG. 10, FIG. 10 is a schematic flowchart of an identification process of whether the physiological signal A and the physiological signal B are homologous. As shown in FIG. 10, after signal data of the physiological signal A and the physiological signal B is detected, first, single-signal analysis (namely, signal preprocessing, feature data extraction, signal quality parameter calculation, and single-signal parameter calculation) is performed on the detected signal data of the physiological signal A and the detected signal data of the physiological signal B; then, waveform matching is performed to determine waveform matching information between the signal data of the two physiological signals, a corresponding associative feature is determined according to the waveform matching information, and a homology reference coefficient between the physiological signal A and the physiological signal B is calculated; and finally, it is decided whether the physiological signal A and the physiological signal B are homologous according to the homology reference coefficient. Further, FIG. 11 shows the constitution of modules in the aforementioned identification process of whether the physiological signal A and the physiological signal B are homologous, namely, a signal monitoring module, a single-signal analysis module, and a signal homology analysis module.

Figure 12:
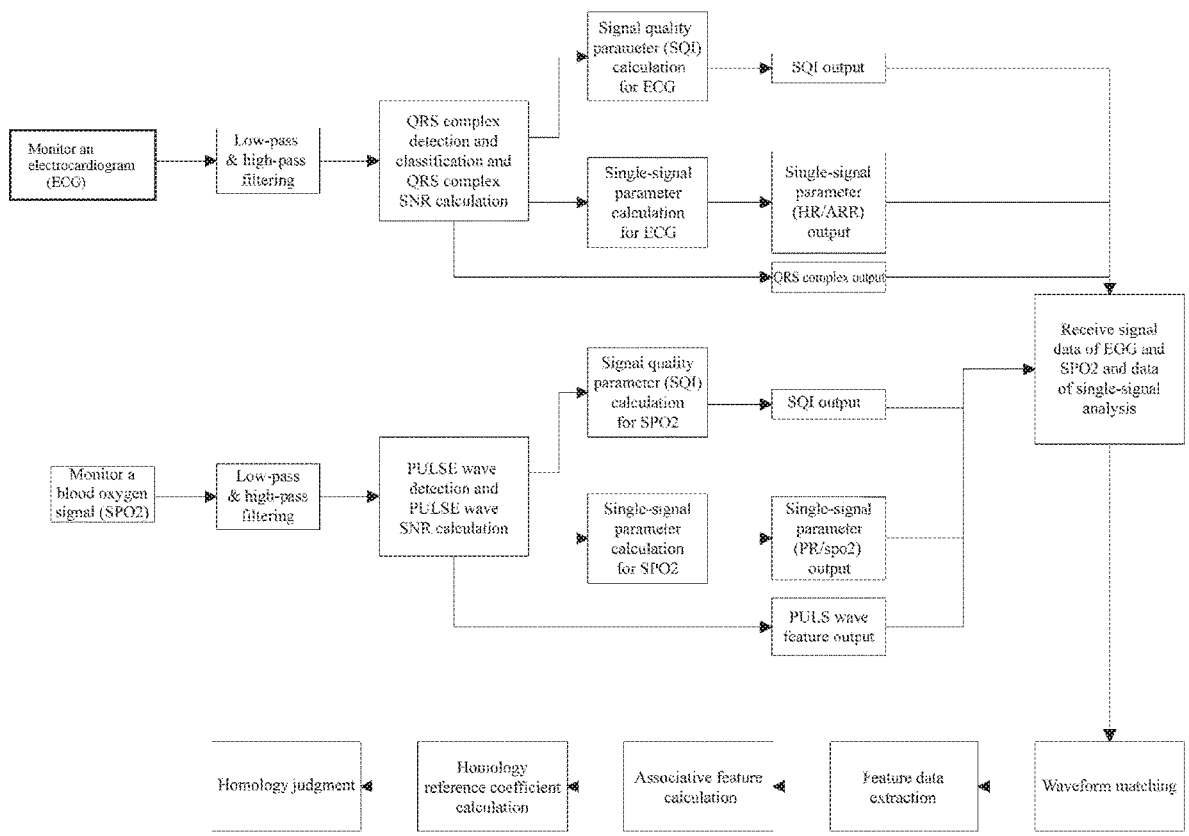
FIG. 12 is a schematic flowchart of identification of whether an electrocardiogram and a blood oxygen signal are homologous in one embodiment.

In one specific embodiment, the physiological signal A is an electrocardiogram (ECG), the physiological signal B is a blood oxygen signal (SPO2), and the process of identifying whether the electrocardiogram and the blood oxygen signal detected by the monitor are homologous may be shown in FIG. 12.

It should be noted that in this embodiment, the process of deciding whether signal data of two different types of physiological signals is homologous may be not only deciding whether they are homologous according to a homology reference coefficient, but also making decision according to other feature data of the signal data of the two different types of physiological signals.

Figure 13:
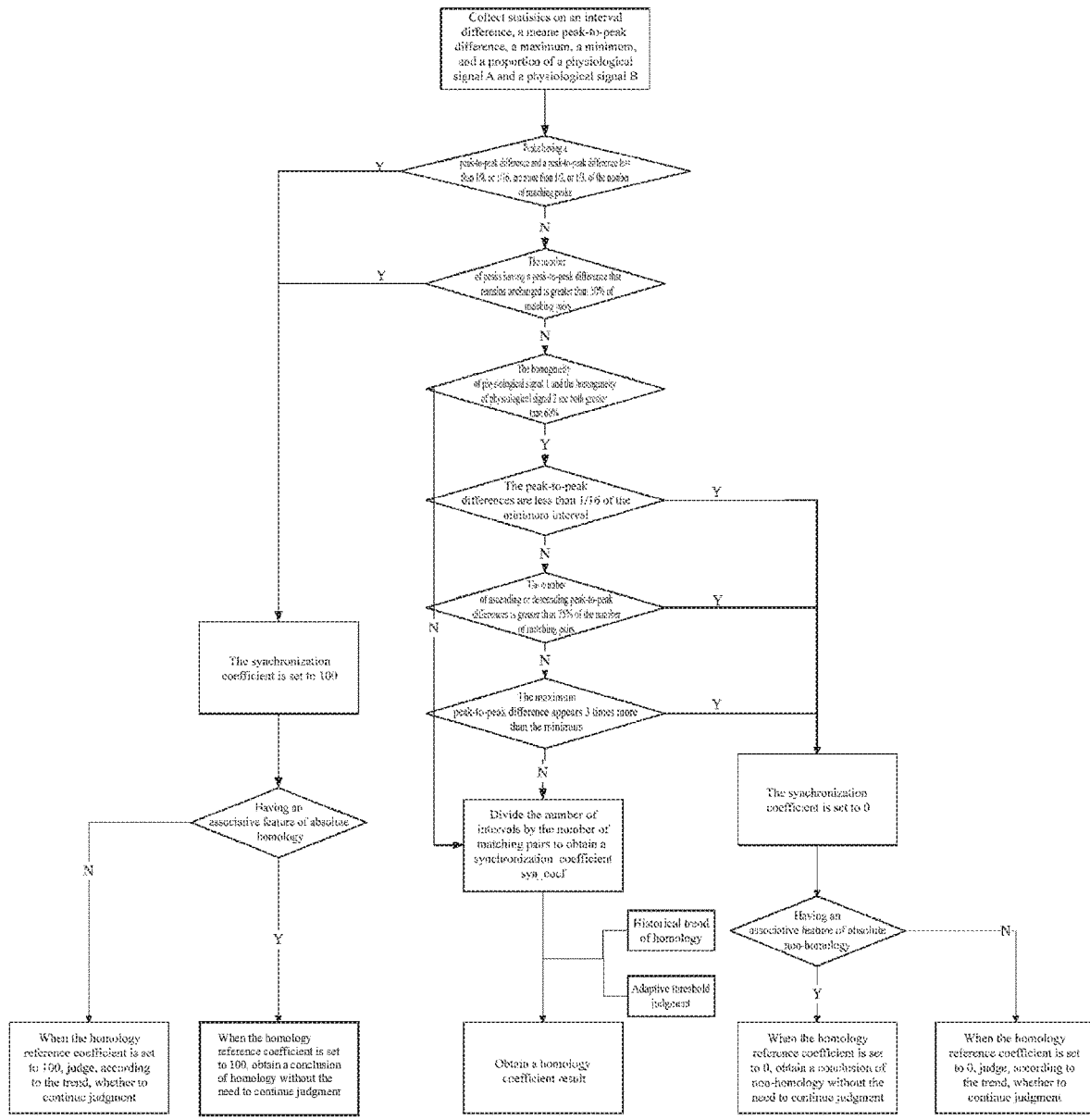
FIG. 13 is a schematic diagram of a homology analysis process on two different types of physiological signals in one embodiment.

In one specific embodiment, as shown in FIG. 13, in addition to acquiring feature data, signal quality parameters, single-signal parameters, an associative feature, and a homology reference coefficient corresponding to the signal data of the physiological signals, an interval difference (a difference between change cycle lengths of two waveforms in the same physiological signal), a mean peak-to-peak difference (an average of differences between timestamps corresponding to peaks of the physiological signal A and peaks of the physiological signal B), a maximum (a maximum of the differences between the timestamps corresponding to the peaks of the physiological signal A and the peaks of the physiological signal B), a minimum (a minimum of the differences between the timestamps corresponding to the peaks of the physiological signal A and the peaks of the physiological signal B), and a proportion of the physiological signal A and the physiological signal B may further be acquired. It should be noted that in the decision process of deciding whether two different types of physiological signals are homologous, acquired parameters are not limited to the parameters listed above, and may further include other parameters or feature data that can show a homology relationship between two pieces of signal data.

As shown in FIG. 13, it is decided step by step whether waveform data of the physiological signal A and waveform data of the physiological signal B are synchronous according to features such as whether specific values of a number of peak-to-peak differences between the physiological signal A and the physiological signal B remain unchanged, whether the peak-to-peak differences are less than a preset interval length, and the difference between the maximum and the minimum. In the case of absolute synchronization, the homology reference coefficient is directly set to 100, that is, the physiological signal A and the physiological signal B are homologous. In the case of absolute non-synchronization, the homology reference coefficient is directly set to 0, that is, the physiological signal A and the physiological signal B are non-homologous. In the case of incomplete synchronization, a proportion of synchronous peaks between peak data of the physiological signal A and peak data of the physiological signal B is calculated according to change rules of the peak-to-peak differences, and it is determined whether the physiological signal A and the physiological signal B are homologous according to the proportion and historical data of homology decision.

Figure 14:
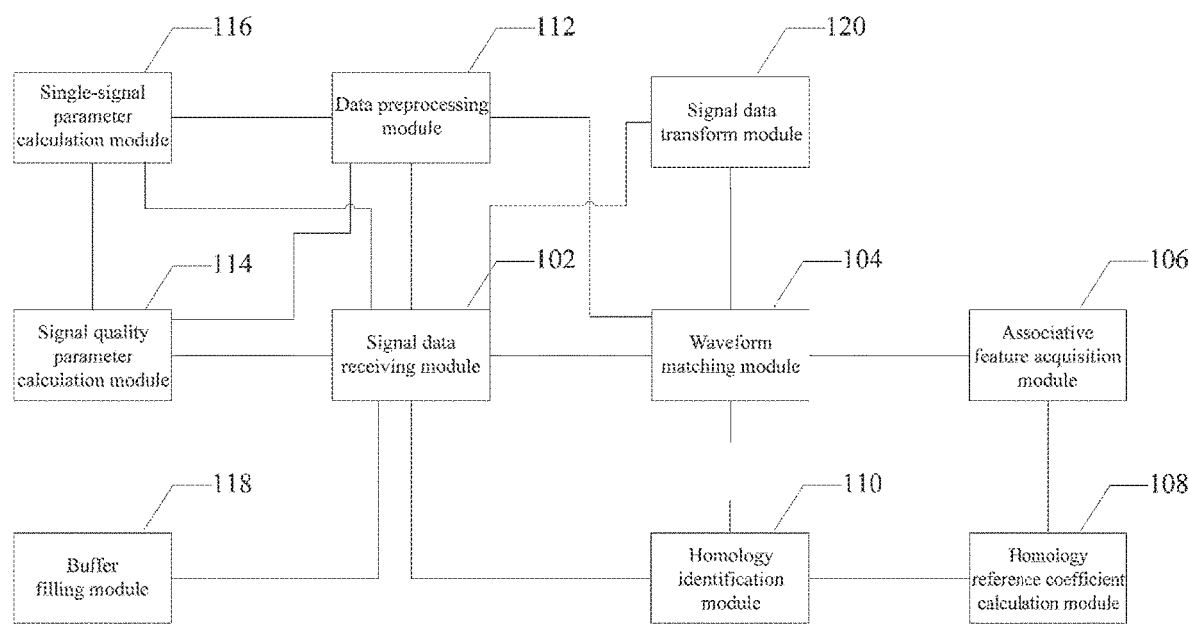
FIG. 14 is a schematic structural diagram of an apparatus for identifying homology of physiological signals in one embodiment.

In addition, to solve the technical problem of low reliability due to the fact that while performing multi-parameter fusional analysis on a plurality of physiological signals detected by a monitor, whether the current plurality of physiological signals originate from the same patient cannot be determined, as shown in FIG. 14, an apparatus for identifying homology of physiological signals is further provided in one embodiment of the disclosure, including a signal data receiving module 102, a waveform matching module 104, an associative feature acquisition module 106, a homology reference coefficient calculation module 108, and a homology identification module 110.

The signal data receiving module 102 is configured to receive signal data of two different types of physiological signals.

The waveform matching module 104 is configured to perform waveform matching on the signal data of the two different types of physiological signals to determine waveform matching information in the signal data of the two types of physiological signals.

The associative feature acquisition module 106 is configured to calculate an associative feature between the signal data of the two different types of physiological signals according to the waveform matching information.

The homology reference coefficient calculation module 108 is configured to calculate a homology reference coefficient corresponding to the two different types of physiological signals according to the associative feature.

The homology identification module 110 is configured to determine that the two different types of physiological signals are homologous when the homology reference coefficient is greater than a preset value.

Optionally, in one embodiment, the associative feature acquisition module 106 is further configured to determine matching peaks in the two different types of physiological signals according to the waveform matching information; calculate a difference sequence of time points corresponding to the matching peaks in the two different types of physiological signals; and use the difference sequence as the associative feature between the signal data of the two different types of physiological signals.

Optionally, as shown in FIG. 14, in one embodiment, the apparatus further includes a data preprocessing module 112, configured to perform high-pass filtering and low-pass filtering on the signal data of the two different types of physiological signals.

Optionally, as shown in FIG. 14, in one embodiment, the apparatus further includes a signal quality parameter calculation module 114, configured to separately extract feature data of the signal data of the two different types of physiological signals; calculate a signal quality parameter corresponding to the feature data according to a preset signal quality parameter calculation formula; when the signal quality parameter does not meet a preset signal quality parameter threshold, determine that the signal data of the physiological signal corresponding to the signal quality parameter is invalid; and when the signal quality parameter meets the preset signal quality parameter threshold, invoke the waveform matching module 104.

Optionally, as shown in FIG. 14, in one embodiment, the apparatus further includes a single-signal parameter calculation module 116, configured to, for any type of physiological signal, determine a signal type of the physiological signal, and determine a single-signal parameter type corresponding to the signal type; calculate a single-signal parameter corresponding to the physiological signal according to a preset single-signal parameter calculation formula and the feature data; decide whether the single-signal parameter meets a preset single-signal parameter threshold; when the single-signal parameter meets the preset single-signal parameter threshold, execute the operation of performing waveform matching on the signal data of the two different types of physiological signals; and when the single-signal parameter does not meet the preset single-signal parameter threshold, generate prompt information of signal abnormality and prompt a user.

Optionally, as shown in FIG. 14, in one embodiment, the apparatus further includes a buffer filling module 118, configured to, for the signal data of the two different types of physiological signals, decide whether a data volume size of the signal data is greater than or equal to a preset data volume threshold, and when the data volume size of the signal data is greater than or equal to the preset data volume threshold, invoke the waveform matching module 104; when the data volume size of the signal data is less than the preset data volume threshold, invoke the signal data receiving module 102.

Optionally, in one embodiment, the homology reference coefficient calculation module 108 is further configured to calculate the homology reference coefficient corresponding to the two different types of physiological signals according to a preset homology reference coefficient calculation formula and the difference sequence.

Optionally, in one embodiment, the homology reference coefficient calculation module 108 is further configured to calculate a mean or mean square error of the difference sequence to serve as the homology reference coefficient corresponding to the two different types of physiological signals.

Optionally, as shown in FIG. 14, in one embodiment, the apparatus further includes a signal data transform module 120, configured to separately perform Fourier transform on the signal data of the two different types of physiological signals to obtain transformed signal data; and the waveform matching module is further configured to perform waveform matching on the transformed signal data corresponding to the signal data of the two different types of physiological signals.

The implementation of the embodiments of the present disclosure will have the following beneficial effects:

by adopting the aforementioned method and apparatus for identifying homology of physiological signals, when a monitor detects signal data of a plurality of different types of physiological signals, an associative feature of the detected signal data of the different types of physiological signals is extracted and calculated to determine the magnitude of a homology reference parameter that can identify the likelihood of two different types of physiological signals being homologous, so as to decide whether the two physiological signals are homologous. That is, homology analysis can be automatically performed on a plurality of items of data detected by the monitor, so as to avoid inaccurate analysis results caused by the fact that whether the detected data originates from the same patient cannot be determined while performing fusional analysis on a plurality of items of data detected by the monitor when the monitor simultaneously detects physiological data of different patients, thereby improving the accuracy and reliability of data analysis results.

The aforementioned embodiments may be implemented in entirety or in part by means of software, hardware, firmware, or any combination thereof. When the embodiments are implemented by means of software programs, they may be implemented in entirety or in part in the form of a computer program product. The computer program product includes one or a plurality of computer instructions. When the computer program instructions are loaded and executed in a computer, the flows or functions described according to the embodiments of the present disclosure are generated in entirety or in part. The computer may be a general computer, a dedicated computer, a computer network, or any other programmable device. The computer instructions may be stored in a computer-readable storage medium or transmitted from one computer-readable storage medium to another computer-readable storage medium. For example, the computer instructions may be transmitted from one website, computer, server, or data center to another website, computer, server, or data center in a wired (for example, a coaxial cable, an optical fiber, or a digital subscriber line (DSL)) or a wireless (for example, infrared, radio, or microwave) manner. The computer-readable storage medium may be any available medium accessible by a computer, or a data storage device including a server, a data center, or the like that has one or a plurality of available media integrated therein. The available medium may be a magnetic medium (for example, a floppy disk, a hard disk, or a magnetic tape), an optical medium (for example, a DVD), a semiconductor medium (for example, a solid state disk (SSD)), or the like.

Figure 15:
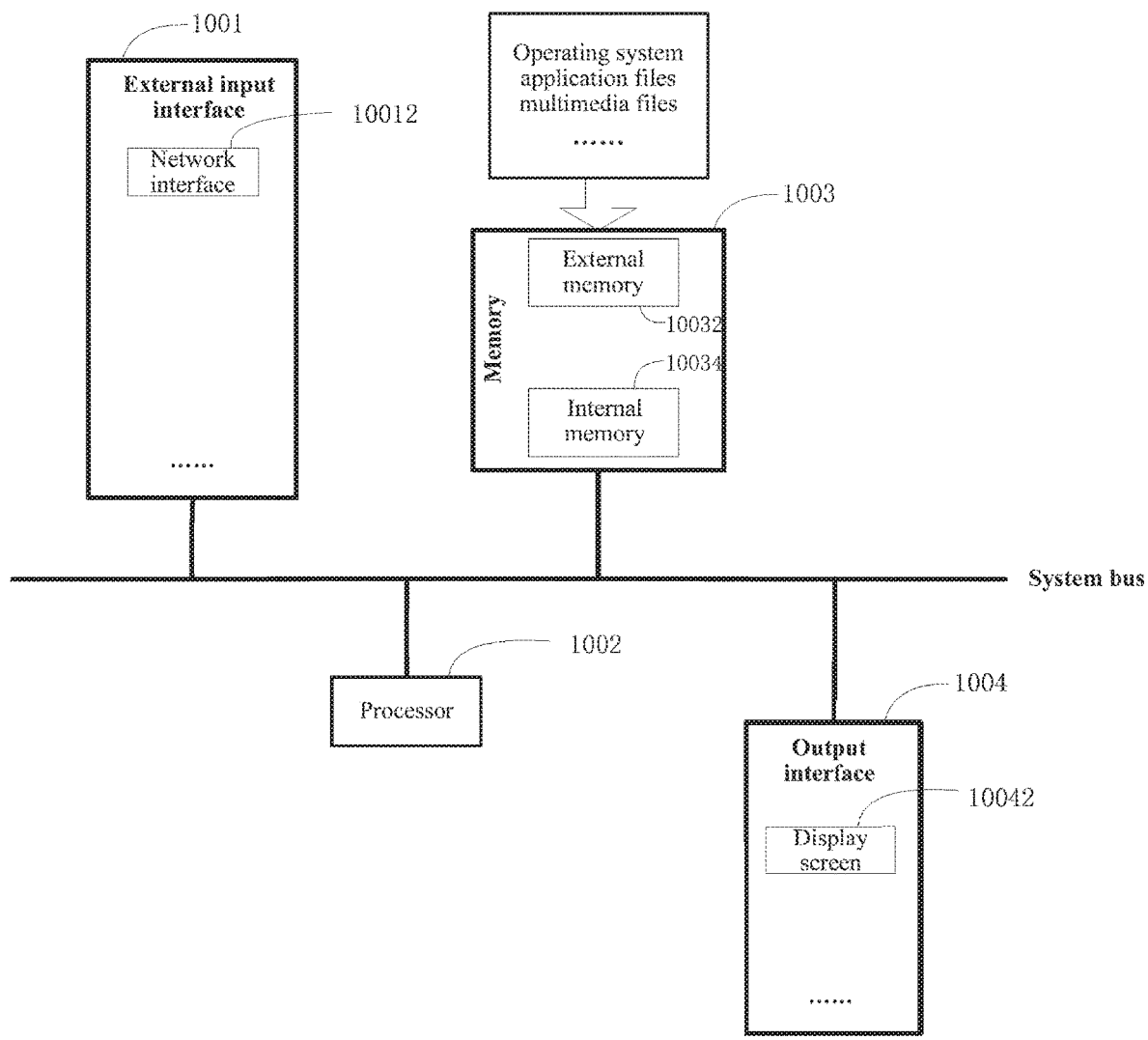
FIG. 15 is a schematic structural diagram of a computer device for running the aforementioned method for identifying homology of physiological signals in one embodiment.

In one embodiment, as shown in FIG. 15, FIG. 15 shows a terminal of a computer system based on a Von Neumann architecture for running the aforementioned method for identifying homology of physiological signals. The computer system may be a terminal device such as a smartphone, a tablet computer, a palm computer, a notebook computer, or a personal computer. Specifically, the computer system may include an external input interface 1001, a processor 1002, a memory 1003, and an output interface 1004 that are connected through a system bus. The external input interface 1001 may optionally include at least a network interface 10012. The memory 1003 may include an external memory 10032 (for example, a hard disk, an optical disc, or a floppy disk) and an internal memory 10034. The output interface 1004 may include at least a device such as a display screen 10042.

In this embodiment, the running of this method is based on a computer program. A program file of the computer program is stored in the external memory 10032 of the computer system based on the Von Neumann architecture, loaded into the internal memory 10034 during running, and afterwards, compiled into machine code and then transferred to the processor 1002 for execution, so as to logically form in the computer system based on the Von Neumann architecture a signal data receiving module 102, a waveform matching module 104, an associative feature acquisition module 106, a homology reference coefficient calculation module 108, a homology identification module 110, a data preprocessing module 112, a signal quality parameter calculation module 114, a single-signal parameter calculation module 116, and a buffer filling module 118. Moreover, in the process of executing the aforementioned method for identifying homology of physiological signals, input parameters are all received through the external input interface 1001, transferred to the memory 1003 for buffering, and then input to the processor 1002 for processing. The result data of processing is either buffered in the memory 1003 for subsequent processing or transferred to the output interface 1004 for output.

Specifically, the processor 1002 is configured to execute the following operations:

receiving signal data of two different types of physiological signals;

performing waveform matching on the signal data of the two different types of physiological signals to determine waveform matching information in the signal data of the twotypes of physiological signals;

calculating an associative feature between the signal data of the two different types of physiological signals according to the waveform matching information;

calculating a homology reference coefficient corresponding to the two different types of physiological signals according to the associative feature; and determining that the two different types of physiological signals are homologous when the homology reference coefficient is greater than a preset value.

Optionally, in one embodiment, the processor 1002 is further configured to determine matching peaks in the two different types of physiological signals according to the waveform matching information; calculate a difference sequence of time points corresponding to the matching peaks in the two different types of physiological signals; and use the difference sequence as the associative feature between the signal data of the two different types of physiological signals.

Optionally, in one embodiment, the processor 1002 is further configured to execute high-pass filtering and low-pass filtering on the signal data of the two different types of physiological signals.

Optionally, in one embodiment, the processor 1002 is further configured to separately extract feature data of the signal data of the two different types of physiological signals; calculate a signal quality parameter corresponding to the feature data according to a preset signal quality parameter calculation formula; when the signal quality parameter does not meet a preset signal quality parameter threshold, determine that the signal data of the physiological signal corresponding to the signal quality parameter is invalid; and when the signal quality parameter meets the preset signal quality parameter threshold, perform the operation of performing waveform matching on the signal data of the two different types of physiological signals.

Optionally, in one embodiment, the processor 1002 is further configured to, for any type of physiological signal, determine a signal type of the physiological signal, and determine a single-signal parameter type corresponding to the signal type; calculate a single-signal parameter corresponding to the physiological signal according to a preset single-signal parameter calculation formula and the feature data; decide whether the single-signal parameter meets a preset single-signal parameter threshold; and when the single-signal parameter does not meet the preset single-signal parameter threshold, generate prompt information of signal abnormality and prompt a user.

Optionally, in one embodiment, the processor 1002 is further configured to, for the signal data of the two different types of physiological signals, decide whether a data volume size of the signal data is greater than or equal to a preset data volume threshold, and if yes, then execute the operation of performing waveform matching on the signal data of the two different types of physiological signals; if not, then continue executing the operation of receiving signal data of two different types of physiological signals.

Optionally, in one embodiment, the processor 1002 is further configured to calculate the homology reference coefficient corresponding to the two different types of physiological signals according to a preset homology reference coefficient calculation formula and the difference sequence.

Optionally, in one embodiment, the processor 1002 is further configured to calculate a mean or mean square error of the difference sequence to serve as the homology reference coefficient corresponding to the two different types of physiological signals.

Optionally, in one embodiment, the processor 1002 is further configured to separately perform Fourier transform on the signal data of the two different types of physiological signals to obtain transformed signal data; and perform waveform matching on the transformed signal data corresponding to the signal data of the two different types of physiological signals.

The above disclosure is merely preferred embodiments of the present disclosure, and certainly not to limit the patentable scope of the present disclosure. Therefore, equivalent changes made according to the claims of the present disclosure still fall within the scope of the present disclosure.

The invention claimed is:

1. A method for identifying homology of physiological signals, comprising:
   detecting two different types of physiological signals by a medical monitor detecting a plurality of types of physiological signals of a plurality of targets, the physiological signals being in a form of waveform;
   matching the two different types of physiological signals to determine waveform matching information in the signal data of the two different types of physiological signals;
   calculating an associative feature between the two different types of physiological signals according to the waveform matching information,
   calculating a homology reference coefficient corresponding to the two different types of physiological signals according to the associative feature; and
   determining that the two different types of physiological signals are from a same target when the homology reference coefficient is greater than a preset value.

2. The method for identifying homology of physiological signals according to claim 1, wherein calculating an associative feature between the signal data of the two different types of physiological signals according to the waveform matching information comprises:
   determining matching peaks in the two different types of physiological signals according to the waveform matching information;
   calculating a difference sequence of time points corresponding to the matching peaks in the two different types of physiological signals; and
   using the difference sequence as the associative feature between the signal data of the two different types of physiological signals.

3. The method for identifying homology of physiological signals according to claim 1, wherein, after receiving signal data of two different types of physiological signals, the method further comprises:
   performing high-pass filtering and low-pass filtering on the signal data of the two different types of physiological signals.

4. The method for identifying homology of physiological signals according to claim 1, wherein, after receiving signal data of two different types of physiological signals, the method further comprises:
   separately extracting feature data of the signal data of the two different types of physiological signals;
   calculating a signal quality parameter corresponding to the feature data according to a preset signal quality parameter calculation formula;
   determining that the signal data of the physiological signal corresponding to the signal quality parameter is invalid when the signal quality parameter does not meet a preset signal quality parameter threshold; and
   performing the waveform matching on the signal data of the two different types of physiological signals when the signal quality parameter meets the preset signal quality parameter threshold.

5. The method for identifying homology of physiological signals according to claim 4, wherein, after separately extracting feature data of the signal data of the two different types of physiological signals, the method further comprises:
   for any type of physiological signal, determining a signal type of the physiological signal, and determining a single-signal parameter type corresponding to the signal type;
   calculating a single-signal parameter corresponding to the physiological signal according to a preset single-signal parameter calculation formula and the feature data;
   deciding whether the single-signal parameter meets a preset single-signal parameter threshold; and
   generating prompt information of signal abnormality and prompting a user when the single-signal parameter does not meet the preset single-signal parameter threshold.

6. The method for identifying homology of physiological signals according to claim 1, wherein, before the performing waveform matching on the signal data of the two different types of physiological signals, the method further comprises:
   for the signal data of the two different types of physiological signals, deciding whether a data volume size of the signal data is greater than or equal to a preset data volume threshold;
   if the data volume size of the signal data is greater than or equal to the preset data volume threshold, performing the waveform matching on the signal data of the two different types of physiological signals; and if the data volume size of the signal data is not greater than or equal to the preset data volume threshold, continuing to receive signal data of two different types of physiological signals.

7. The method for identifying homology of physiological signals according to claim 2, wherein calculating a homology reference coefficient corresponding to the two different types of physiological signals according to the associative feature comprises:

calculating the homology reference coefficient corresponding to the two different types of physiological signals according to a preset homology reference coefficient calculation formula and the difference sequence.

8. The method for identifying homology of physiological signals according to claim 7, wherein calculating a homology reference coefficient corresponding to the two different types of physiological signals according to the associative feature further comprises:

calculating a mean or mean square error of the difference sequence to serve as the homology reference coefficient corresponding to the two different types of physiological signals.

9. The method for identifying homology of physiological signals according to claim 1, wherein, before the performing waveform matching on the signal data of the two different types of physiological signals, the method further comprises:

separately performing Fourier transform on the signal data of the two different types of physiological signals to obtain transformed signal data; and performing the waveform matching on the transformed signal data corresponding to the signal data of the two different types of physiological signals.

10. An apparatus for identifying homology of physiological signals, comprising:

a signal data receiving module, configured to detect two different types of physiological signals by a medical monitor detecting a plurality of types of physiological signals of a plurality of targets, the physiological signals being in a form of waveform;

a waveform matching module, configured to match the two different types of physiological signals to determine waveform matching information the two different types of physiological signals;

an associative feature acquisition module, configured to calculate an associative feature between the two different types of physiological signals according to the waveform matching information;

a homology reference coefficient calculation module, configured to calculate a homology reference coefficient corresponding to the two different types of physiological signals according to the associative feature; and a homology identification module, configured to determine that the two different types of physiological signals are from a same target when the homology reference coefficient is greater than a preset value.

11. The apparatus for identifying homology of physiological signals according to claim 10, wherein associative feature acquisition module is further configured to:

determine matching peaks in the two different types of physiological signals according to the waveform matching information;

calculate a difference sequence of time points corresponding to the matching peaks in the two different types of physiological signals; and use the difference sequence as the associative feature between the signal data of the two different types of physiological signals.

12. The apparatus for identifying homology of physiological signals according to claim 10, wherein the apparatus further comprises:

a data preprocessing module, configured to perform high-pass filtering and low-pass filtering on the signal data of the two different types of physiological signals.

13. The apparatus for identifying homology of physiological signals according to claim 10, wherein the apparatus further comprises a signal quality parameter calculation module, configured to:

separately extract feature data of the signal data of the two different types of physiological signals;

calculate a signal quality parameter corresponding to the feature data according to a preset signal quality parameter calculation formula;

determine that the signal data of the physiological signal corresponding to the signal quality parameter is invalid when the signal quality parameter does not meet a preset signal quality parameter threshold; and invoke the waveform matching module when the signal quality parameter meets the preset signal quality parameter threshold.

14. The apparatus for identifying homology of physiological signals according to claim 13, wherein the apparatus further comprises a single-signal parameter calculation module, configured to:

for any type of physiological signal, determine a signal type of the physiological signal, and determine a single-signal parameter type corresponding to the signal type;

calculate a single-signal parameter corresponding to the physiological signal according to a preset single-signal parameter calculation formula and the feature data;

decide whether the single-signal parameter meets a preset single-signal parameter threshold; and generate prompt information of signal abnormality and prompt a user when the single-signal parameter does not meet the preset single-signal parameter threshold.

15. The apparatus for identifying homology of physiological signals according to claim 10, wherein the apparatus further comprises a buffer filling module, configured to:

for the signal data of the two different types of physiological signals, decide whether a data volume size of the signal data is greater than or equal to a preset data volume threshold;

when the data volume size of the signal data is greater than or equal to the preset data volume threshold, invoke the waveform matching module; and when the data volume size of the signal data is less than the preset data volume threshold, invoke the signal data receiving module.

16. The apparatus for identifying homology of physiological signals according to claim 11, wherein the homology reference coefficient calculation module is further configured to calculate the homology reference coefficient corresponding to the two different types of physiological signals according to a preset homology reference coefficient calculation formula and the difference sequence.

17. The apparatus for identifying homology of physiological signals according to claim 16, wherein the homology reference coefficient calculation module is further configured to calculate a mean or mean square error of the difference sequence to serve as the homology reference coefficient corresponding to the two different types of physiological signals.

18. The apparatus for identifying homology of physiological signals according to claim 10,
   wherein the apparatus further comprises a signal data transform module, configured to separately perform Fourier transform on the signal data of the two different types of physiological signals to obtain transformed signal data,
   wherein the waveform matching module is further configured to perform the waveform matching on the transformed signal data corresponding to the signal data of the two different types of physiological signals.

19. A computer-readable storage medium, comprising computer instructions, when executed by a computer, causing the computer to perform the method according to claim 1.

20. A terminal for identifying homology of physiological signals, comprising:
   a processor and a memory, wherein
   the processor performs the method according to claim 1 by executing a calling code or instructions in the memory.

21. The method according to claim 1, wherein the waveform matching information is indicative of a degree of synchronization between the waveforms of the two different types of physiological signals, and the homology reference coefficient is corresponding to a proportion of synchronous peaks between the two different types of physiological signals.

* * * * *